United States Patent [19]

Heise et al.

[11] Patent Number: 5,047,586
[45] Date of Patent: Sep. 10, 1991

[54] PROCESS FOR THE PREPARATION OF 4-ACYLAMINO-2-AMINOALKOXYBENZENES

[75] Inventors: Hartmut Heise, Bad Soden am Taunus; Manfred Hintzmann, Hofheim am Taunus, both of Fed. Rep. of Germany

[73] Assignee: Hoechst Aktiengesellschaft, Frankfurt am Main, Fed. Rep. of Germany

[21] Appl. No.: 571,505

[22] Filed: Aug. 22, 1990

Related U.S. Application Data

[63] Continuation of Ser. No. 308,883, Feb. 9, 1989.

[30] Foreign Application Priority Data

Feb. 13, 1988 [DE] Fed. Rep. of Germany ....... 3804621

[51] Int. Cl.$^5$ ................. C07C 231/02; C07C 209/36
[52] U.S. Cl. .................................... 564/144; 564/418
[58] Field of Search ............................. 564/144, 418

[56] References Cited

U.S. PATENT DOCUMENTS

| | | | |
|---|---|---|---|
| 2,478,114 | 8/1949 | Lind et al. | 260/562 |
| 3,928,451 | 12/1975 | Krishnan | 260/580 |
| 4,288,592 | 9/1981 | Rauhut et al. | 544/159 |
| 4,320,021 | 3/1982 | Lange | 252/51.5 R |

FOREIGN PATENT DOCUMENTS

| | | |
|---|---|---|
| 0011048 | 1/1982 | European Pat. Off. |
| 1543625 | 4/1973 | Fed. Rep. of Germany |
| 0933174 | 8/1963 | United Kingdom |
| 1522273 | 8/1978 | United Kingdom |

Primary Examiner—Glennon H. Hollrah
Assistant Examiner—P. G. O'Sullivan

[57] ABSTRACT

A process for the preparation of 4-acylamino-2-aminoalkoxybenzenes of the general formula (1)

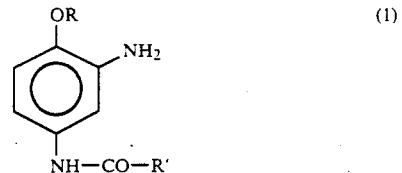

in which R denotes an alkyl-$C_1$-$C_6$- or alkoxy-$C_1$-$C_4$-alkylene-$C_1$-$C_4$ group and R' denotes a methyl or ethyl group, by pumping a solution or suspension of a 2,4-dinitroalkoxybenzene of the general formula (2)

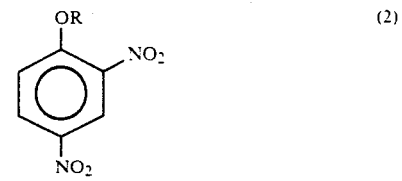

in which R has the abovementioned meaning, in a butyl acetate into a stirred suspension of a nickel catalyst on a kieselguhr carrier in butyl acetate, which has been initially introduced into an autoclave, at a hydrogen pressure of about 5 to about 50 bar, and a temperature of about 60° to about 120° C., at a rate which corresponds to the rate of hydrogenation of 2,4-dinitroalkoxybenzene to 2,4-diaminoalkoxybenzene, dehydrating the reduction solution by azeotropic distillation, after the hydrogenation, and acylating the resulting 2,4-diaminoalkoxybenzene with about 0.90 to 0.99 mole of the anhydride of an alkylmonocarboxylic acid having 2 to 3 carbon atoms, relative to 1 mole of 2,4-diaminoalkoxybenzene, at about −5° to about +15° C.

8 Claims, No Drawings

PROCESS FOR THE PREPARATION OF 4-ACYLAMINO-2-AMINOALKOXYBENZENES

This application is a continuation of copending application Ser. No. 07/308,883 filed on Feb. 9, 1989.

The invention relates to an improved process compared with the prior art for the preparation of 4-acylamino-2-aminoalkoxybenzenes by catalytic hydrogenation of 2,4-dinitroalkoxybenzenes in butyl acetate over a nickel catalyst to give 2,4-diaminoalkoxybenzenes followed by selective acylation thereof.

The principle of the preparation of 4-acylamino-2-aminoalkoxybenzenes from 2,4-dinitroalkoxybenzenes is known (EP 0,011,048). The reduction (hydrogenation) of the dinitroalkoxybenzenes described there is carried out in an alcoholic suspension in a hydrogen atmosphere in the presence of noble metal catalysts. The control of this strongly exothermic reaction is difficult, especially since a temperature of 60° C. should not be exceeded in order to avoid the formation of tar-like byproducts. If it is desired to adhere to this temperature limit, the reduction is only allowed to proceed slowly, since otherwise it is not possible to remove the heat of reduction of 2 nitro groups which is liberated. This means long reaction times and accordingly a long lifetime of reduction intermediates which in turn can undergo a reaction owing to the steric proximity of the two substituents which react and lead to the increased formation of byproducts.

Likewise it is known that the lifetime of reduction intermediates and accordingly the possibility of forming undesired byproducts is affected by the solvent used [JACS 74 (1952) 1297]. Thus, it has been shown that for the reduction (hydrogenation) of 2,4-dinitrobenzene compounds water is highly unsuitable as solvent.

Better results are obtained with alcohols, such as methanol or ethanol. Alkyl acetates have proven to be particularly suitable as solvents. The smallest amounts of byproducts are observed in catalytic reductions (hydrogenations) using these solvents. Thus, in particular ethyl acetate alone or in a mixture with alcohols, such as methanol or ethanol, has been used as solvent for catalytic reductions of 2,4-dinitrotoluene (German Offenlegungsschrift 2,428,141).

Also known is the process variation in which the lifetime of reduction intermediates is shortened by pumping the solution or suspension of the dinitrobenzene compound to a stirred catalyst suspension initially introduced into an autoclave under a hydrogen atmosphere (German Offenlegungsschrift 2,732,409; U.S. Pat. No. 3,154,584).

The catalysts used for the reduction (hydrogenation) of aromatic 2,4-dinitrobenzene compounds are almost exclusively noble metal catalysts, such as platinum or palladium on charcoal carriers or Raney nickel, since only catalysts of this type make reduction (hydrogenation) at low temperatures possible (EP 0,011,048; JP-OS 81/45,445). If, however, nickel catalysts on kieselguhr carriers are used, significantly higher hydrogenation temperatures are required, which specifically in the case of dinitro compounds, due to the mutual interaction of the reduction intermediates in the conventional hydrogenation process, lead to a significantly higher percentage of byproducts and accordingly to a reduction in yield.

The selective acylation which follows the catalytic reduction (hydrogenation) has likewise been described (EP 0,011,048; UK Patent 1,324,303; JA-OS 78/15,328; JA-OS 80/167,264; JA-OS 81/45,445; JA-OS 84/65,054). In this reaction, diaminoalkoxybenzene and acylating agents are always used in an equimolar ratio or with an excess of acylating agent. The additives used, which are said to affect the selectivity favorably, are inter alia magnesium oxide or a mixture of dialkylamine and acetic acid. The acylation is carried out in the solvent in which the catalytic reduction (hydrogenation) took place.

Not only the desired 4-acylamino-2-aminophenyl ethers are formed in the acylation of 2,4-diaminophenyl ethers, but the reaction mixture additionally always contains portions of unconverted starting compound and of bis-acylated compound.

Surprisingly, it has now been found that 4-acylamino-2-aminoalkoxybenzenes of the general formula (1)

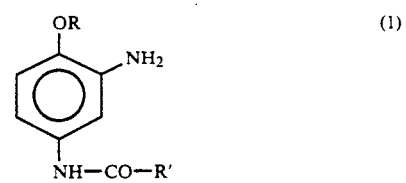

in which R denotes an alkyl-$C_1$-$C_6$- or alkoxy-$C_1$-$C_4$-alkylene-$C_1$-$C_4$ group and R' denotes a methyl or ethyl group, can be prepared advantageously in a higher yield and better quality by pumping a solution or suspension of a 2,4-dinitroalkoxybenzene of the general formula (2)

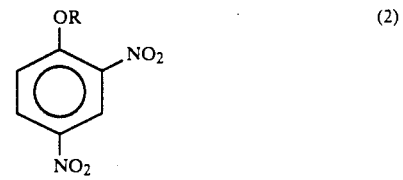

in which R has the abovementioned meaning, in a butyl acetate into a stirred suspension of a nickel catalyst on a kieselguhr carrier butyl acetate, which has been initially introduced into an autoclave, at a hydrogen pressure of about 5 to about 50 bar, preferably about 30 to about 40 bar, and a temperature of about 60° to about 120° C., preferably about 80° to about 110° C., at a rate which corresponds to the rate of the hydrogenation of 2,4-dinitroalkoxybenzene to 2,4-diaminoalkoxybenzene, dehydrating the reduction solution azeotropically after the hydrogenation is completed, and acylating the resulting 2,4-diaminoalkoxybenzene with the anhydride of an alkylmonocarboxylic acid having 2 to 3 carbon atoms at a temperature of about −5° to about +15° C., preferably about 5° to about 10° C.

Another surprising aspect regarding the two reaction steps is specifically that the use of butyl acetate as solvent or diluent in combination with metering of the solution or suspension of 2,4-dinitroalkoxybenzene to the stirred catalyst suspension, which is present in a hydrogen atmosphere, leads to significantly improved quality and yield of 2,4-diaminoalkoxybenzene or 4-acylamino-2-aminoalkoxybenzene, in which reaction the metering rate should correspond to the hydrogenation rate, that is, the reduction (hydrogenation) to the diamine should occur spontaneously and intermediate stages of reduction should be passed through at such a rate that mutual interactions are excluded.

It must furthermore be considered surprising that these advantages can be obtained using a nickel catalyst on a kieselguhr carrier, specifically at temperatures between about 60° and about 120° C., which in conventional hydrogenation processes using, for example, alcohol or water as solvent leads to unusable products. It has indeed been shown that the 2,4-diaminoalkoxybenzene, which is formed spontaneously in the embodiment according to the invention, is very stable in the hydrogenation mixture under a hydrogen atmosphere even at elevated temperatures.

Furthermore nickel catalysts (on a kieselguhr carrier) have, compared with noble metal catalysts and Raney nickel, the advantage that they do not self-ignite and can be easily and safely handled in practice. Moreover they are less sensitive to impurities and catalyst poisons and, due to their comparatively low price, it is not necessary to use them several times. The repeated use, for example of noble metal catalysts, requires constant adjustment of the hydrogenation conditions to the catalyst activities which decrease from use to use. In contrast, using the catalyst once leads to the great advantage of always constant reaction conditions, when the process is carried out in practice.

The selective acylation which follows the catalytic reduction is advantageously carried out in the same solvent in which the catalytic reduction took place (butyl acetate). However, since in the catalytic reduction (hydrogenation), 4 mol of water are formed per mole of 2,4-dinitroalkoxybenzene and since water impairs the acylation in terms of yield and selectivity, it is advantageous to dehydrate the resulting reduction solution beforehand. If alcohols are used as solvents (EP 0,011,048; UK Patent 1,324,303), dehydration of the hydrogenation solution is practically impossible. However, if butyl acetate is used as solvent, the water formed in the reduction (hydrogenation) can either be separated off from the mixture as the bottom layer or conveniently removed by azeotropic distillation, the removal by azeotropic distillation being preferred due to the high yield thus obtainable. The use of magnesium oxide as in the process carried out in alcohol can be omitted in the process according to the invention.

A further surprising aspect of the selective acylation is that an excess of acylating agent of up to 10%, relative to the 2,4-diaminoalkoxybenzene, leads to higher yields of 4-acylamino-2-aminoalkoxybenzene. An addition of acylating agent higher than that not only does not cause an increased formation of the target product, but it also brings about a decrease in the yield in favor of the formation of 2,4-bis(acylamino)alkoxybenzene.

The process according to the invention is carried out in detail as follows:

To a suspension of the nickel catalyst (on a kieselguhr carrier) in n-butyl acetate or iso-butyl acetate or in a mixture thereof, which has been initially introduced into an autoclave under a hydrogen pressure of about 5 to about 50 bar, preferably about 30 to about 40 bar, and heated to 80° C., is pumped a solution or suspension of 2,4-dinitroalkoxybenzene in the same solvent, which was used for suspending the catalyst, at a rate which corresponds to the hydrogenation rate of the dinitro to the diamino compound, which can very easily be controlled by the absorption of hydrogen. During the course of the reduction, the temperature increases to 110° C. The catalyst which is used consists of a kieselguhr carrier having up to 60% by weight of nickel and is preferably used in an amount of 1 to 3% by weight, relative to 2,4-dinitroalkoxybenzene.

Before the selective acylation, which takes place in the second reaction step without isolation of the resulting 2,4-diaminoalkoxybenzene intermediate, the reduction solution which has been freed from the catalyst is dehydrated by simple azeotropic distillation. The acylating agent used is preferably acetic or propionic anhydride in an amount of 0.90 to 0.99 mole, preferably 0.93 to 0.96 mole per mole of 2,4-diaminoalkoxybenzene. The acylation takes place at temperatures of about −5° to about +15° C., preferably at about +5° to about +10° C.

The process products of the general formula (1) mentioned represent useful coupling components for the preparation of disperse azo dyes.

The process according to the invention is intended to be illustrated in more detail by the examples which follow, without being limited thereto.

EXAMPLE 1

3 g of nickel catalyst (having about 55% by weight of nickel on a kieselguhr carrier) in 300 ml of n-butyl acetate are placed in a 2 liter hydrogenation autoclave. After flushing with nitrogen, 30 bar of hydrogen are injected, and the catalyst suspension is heated to 80° C. with stirring. The pumping of a solution of 242.2 g of 2,4-dinitromethoxyethoxybenzene in 500 ml of n-butyl acetate into this suspension is then started, specifically at a rate which corresponds to the reduction rate to the diamine, which can be recognized by the termination of the hydrogen absorption directly after interrupting the metering.

During the metering time of about 90 minutes, the temperature increases from 80° C. to about 110° C. despite cooling. After the reduction is completed, the autoclave content is cooled to 40° C. and discharged. The reduction solution freed from the catalyst is then dehydrated azeotropically by removing the water formed during the reaction through a water separator by distillation.

The anhydrous solution of the diamine in n-butyl acetate thus obtained is cooled to 5° C. with stirring. Over a period of 6 hours, 123 g of propionic anhydride are pumped uniformly into the solution, and the temperature is allowed to rise to 10° C. during this time. Workup and drying give 229.7 g of a 98.6% pure product, which corresponds to a yield of 95.2% of theory in 4-propionylamino-2-aminomethoxyethoxybenzene.

According to analysis by HPLC, the content of nonacylated 2,4-diaminomethoxyethoxybenzene is 0.3% and that of 2,4-bis(propionylamino)methoxyethoxybenzene 0.7%.

EXAMPLE 2

The procedure as described in Example 1 is repeated, except that 96.5 g of acetic anhydride instead of 123 g of propionic anhydride are used for the acylation.

Workup and drying give 215.1 g of a 98.3% pure product, which corresponds to a yield of 94.4% of theory in 4-acetylamino-2-aminomethoxyethoxybenzene.

The content of non-acylated 2,4-diaminomethoxyethoxybenzene is 0.8% and that of 2,4-bis(acetylamino)-methoxyethoxybenzene 0.5% (HPLC).

EXAMPLE 3

The procedure as described in Example 1 is repeated, except that 198 g of 2,4-dinitromethoxybenzene instead of 242.2 g of 2,4-dinitromethoxyethoxybenzene and acetic anhydride instead of propionic anhydride are used.

Removal of the catalyst and azeotropic removal of the water of the hydrogenation give 972 g of a 13.9% by weight strength solution of 2,4-diaminomethoxybenzene in butyl acetate, which corresponds to a yield of 97.9% of theory.

Analogously to Example 1, over a period of 6 hours 95.0 g of acetic anhydride are pumped into the stirred diamine solution which has been cooled to 5° C. Workup and drying give 165.8 g of 4-acetylamino-2-aminomethoxybenzene, which corresponds to a yield of 92% of theory. The content of non-acylated 2,4-dinitromethoxybenzene is 0.8% and the content of 2,4-bis-(acetylamino)methoxybenzene 1.2% (HPLC).

EXAMPLE 4

The procedure as described in Example 1 is repeated, except that 226.2 g of 2,4-dinitrophenyl isopropyl ether are used instead of 242.2 g of 2,4-dinitromethoxyethoxybenzene.

Workup and drying give 216.4 g of a 98.4% pure product (m.p. 88°–89° C.), which corresponds to a yield of 95.8% of theory in 4-propionylamino-2-aminophenyl isopropyl ether.

The content of non-acylated 2,4-diaminophenyl isopropyl ether is 0.4% and that of 2,4-bis(propionylamino)phenyl isopropyl ether 0.7% (HPLC).

We claim:

1. A process for the preparation of 4-acylamino-2-aminoalkoxybenzenes of the formula (1)

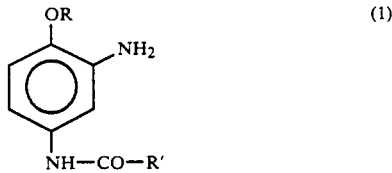

in which R denotes an alkyl-$C_1$-$C_6$- or alkoxy-$C_1$-$C_4$-alkylene-$C_1$-$C_4$ group and R' denotes a methyl or ethyl group, which comprises pumping a solution or suspension of a 2,4-dinitroalkoxybenzene of the formula (2)

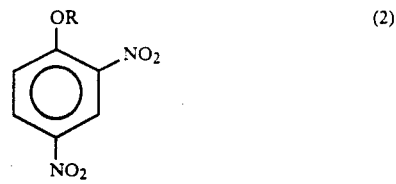

in which R has the above mentioned meaning, in a butyl acetate into a stirred suspension of a nickel catalyst on a kieselguhr carrier in butyl acetate, which has been initially introduced into an autoclave, at a hydrogen pressure of about 5 to about 50 bar, and a temperature of about 60° to about 120° C., at a rate which corresponds to the rate of the hydrogenation of 2,4-dinitroalkoxybenzene to 2,4-diaminoalkoxybenzene, dehydrating the reduction solution by azeotropic distillation, after the hydrogenation is completed, and acylating the resulting 2,4-diaminoalkoxybenzene with about 0.90 to about 0.99 mole of the anhydride of an alkylmonocarboxylic acid having 2 to 3 carbon atoms, relative to 1 mole of 2,4-diaminoalkoxybenzene, at temperatures of about −5° to about +15° C.

2. The process as claimed in claim 1, wherein the hydrogenation and the acylation is carried out in n-butyl acetate or iso-butyl acetate or in a mixture thereof.

3. The process as claimed in claim 1, wherein the hydrogenation is carried out at a hydrogen pressure of about 30 to about 40 bar.

4. The process as claimed in claim 1, wherein the hydrogenation is carried out at a temperature of about 80° to about 110° C.

5. The process as claimed in claim 1, wherein the acylation is carried out at temperatures from about 5° to about 10° C.

6. The process as claimed in claim 1, wherein the alkylmonocarboxylic anhydride for the acylation is used in an amount of about 0.93 to about 0.96 mole, relative to 1 mole of 2,4-diaminoalkoxybenzene.

7. The process as claimed in claim 1, wherein acetic anhydride is used as the acylating agent.

8. The process as claimed in claim 1, wherein propionic anhydride is used as the acylating agent.

* * * * *